United States Patent [19]

Foote et al.

[11] Patent Number: 5,556,961

[45] Date of Patent: Sep. 17, 1996

[54] NUCLEOSIDES WITH 5'-O-PHOTOLABILE PROTECTING GROUPS

[76] Inventors: Robert S. Foote, 105 Elliot Cir., Oak Ridge, Tenn. 37830; Richard A. Sachleben, 1105 Hickory Trail, Knoxville, Tenn. 37932

[21] Appl. No.: 328,079

[22] Filed: Oct. 24, 1994

Related U.S. Application Data

[60] Continuation of Ser. No. 117,783, Sep. 7, 1993, abandoned, which is a division of Ser. No. 794,723, Nov. 15, 1991, abandoned.

[51] Int. Cl.⁶ .................. C07H 19/06; C07H 19/067; C07H 19/073; C07H 19/16
[52] U.S. Cl. .................. 536/27.1; 536/27.6; 536/27.81; 536/28.5; 536/28.54
[58] Field of Search ............................... 536/27.1, 26.11, 536/27.6, 27.81, 28.54, 28.5, 28.4, 27.21

[56] References Cited

U.S. PATENT DOCUMENTS

| | | | |
|---|---|---|---|
| 3,951,748 | 4/1976 | Devlin | 195/103.5 |
| 4,415,732 | 11/1983 | Caruthers et al. | 536/25.33 |
| 4,563,417 | 1/1986 | Albarella et al. | 435/6 |
| 4,591,567 | 5/1986 | Britten et al. | 435/193 |
| 4,724,202 | 2/1988 | Dattagupta et al. | 435/6 |
| 4,731,325 | 3/1988 | Palva et al. | 435/6 |
| 4,755,458 | 7/1988 | Rabbani et al. | 435/5 |
| 4,797,355 | 1/1989 | Stabinsky | 435/6 |
| 4,837,733 | 6/1989 | Shariashi et al. | 364/413.13 |
| 4,868,105 | 9/1989 | Ureda et al. | 536/27 |
| 5,021,550 | 6/1991 | Zeiger | 530/334 |
| 5,112,963 | 5/1992 | Pielas et al. | 536/27 |
| 5,143,854 | 9/1992 | Pirrung et al. | 435/518 |

OTHER PUBLICATIONS

Pillai, Organic Photochemistry, vol. 9, A. Padwa, E. D., Marcel Dekker, Inc., New York, 1987, pp. 225–323.

*Primary Examiner*—Gary L. Kunz
*Attorney, Agent, or Firm*—Luedeka, Neely & Graham, P.C.

[57] ABSTRACT

Nucleosides with photolabile protecting groups on the 5'-hydroxyl. These nucleosides are useful in the sythesis of nucleic acids on solid-state arrays.

6 Claims, 11 Drawing Sheets

MATCH LINE TO FIG. 3B

MATCH LINE TO FIG. 3A

FIG. 3B

MATCH LINE TO FIG. 3C

MATCH LINE TO FIG. 4B

MATCH LINE TO FIG. 4A step g step h ↓ step i ↓ step j ↓ AX step k ↓

MATCH LINE TO FIG. 4C

MATCH LINE TO FIG. 4C step q ↓ step r ↓ step s ↓ TX

NUCLEOSIDES WITH 5'-O-PHOTOLABILE PROTECTING GROUPS

This invention was made with U.S. government support under Contract No. 41B-99732 awarded by the Department of Energy. The U.S. government has certain rights in this invention.

This is a continuation, of application Ser. No. 08/117,783, filed Sep. 7, 1993, now abandoned, which is a division of Ser. No. 07/794,723, filed Nov. 15, 1991, now abandoned.

The present invention relates to solid-state arrays of chemical products, particularly biopolymers and to methods for making solid-state arrays.

Recently, micro-scale solid-state arrays of biopolymers (such as nucleic acids or polypeptides) have been reported in the literature for various analytical and synthetic uses. For example, Foder, et al. (Science, Vol. 251, pp. 767–773 [1991]) observes that such arrays of oligonucleotides would be valuable in gene mapping, fingerprinting, diagnostics, and nucleic acid sequencing.

Solid-state arrays of biopolymers comprise aligned rows and columns of, usually, different biopolymers arranged on the surface of a substrate. These arrays are generally prepared by successively reacting selected portions of the array substrate with selected biomonomers (such as nucleotides or amino acids) in the form of derivatives for solid-phase synthesis.

Southern, in PCT Application WO 89/10977, describes the preparation of an array of oligomeric DNA. The array taught by Southern comprises a collection of, for example, all 256 of the sequences of DNA which are four nucleotides long, and contain the nucleotides of adenine (A), cytosine (C), guanine (G) and thymine (T). The array is prepared on the reactive surface of a substrate, such as a glass plate, which is derivatized with an aliphatic linker bearing a terminal hydroxyl group to which the first base is added. The biomonomers (in this case nucleoside phosphoramidites, which are eventually converted to nucleotides) are applied one at a time to selected portions of the surface. The portions of the surface which are not selected for receiving a biomonomer during a given step of the process are protected by the application of a physical mask, such as silicone rubber, in physical contact with the surface.

For example, Southern teaches that the first four bases of the array may be laid in four broad stripes on the glass plate. The second set of bases is then added in four stripes of equal width to the first and orthogonal to them resulting in a four-by-four array of dimers (AA, AC, AG, etc.). The third and fourth sets are added in stripes one-quarter the width of the first stripes and positioned so that each set of narrow stripes runs within one of the broad stripes, resulting in an array of all 256 tetranucleotides. The process may be repeated using even narrower stripes to produce arrays of longer oligonucleotides.

Although the process of Southern is relatively straightforward, there are significant practical difficulties in the application of the technique to producing arrays of very small micro-scale size (i.e., less than about 2 cm$^2$) with several tens of thousands of cells. For example, an array of 256-by-256 is required to produce an array of all possible sequences of octameric DNA. To prepare such an array 1.5 cm on a side with physical masks demands the repeated positioning of the masks with a precision of greater than 0.06 mm (60 micron). In practice, that level of precision is very difficult to reproduce and sustain throughout the production of a micro-scale array. Therefore, no micro-scale arrays are known to have been produced using the techniques taught by Southern.

A further disadvantage of the array produced in accordance with the method disclosed by Southern relates to background effects. Arrays produced by intersecting stripes will contain individual cells which are surrounded by and border upon regions containing similar, though shorter sequences. When the array is later contacted by an unknown reagent, such as with an unknown nucleic acid under hybridization conditions, interactions may occur to some extent with the intervening sequences, resulting in background noise and reduction in discrimination of accurately hybridized sites.

More specifically, the accuracy and positioning of successive masks during the preparation of arrays on a uniformly functionalized surface do not precisely define the boundaries between the individual locations on the surface of the substrate. As the biomonomers are deposited on the substrate, inaccuracies in and positioning errors of the masks may produce biopolymers on the borders between cells which have sequences significantly different from the sequences in the adjacent cells. These boundary effects produce "border biopolymers" with sequences that are similar, at least in part, to cells remote from the border biopolymers. Therefore, these boundary effects generate "noise" in the array. For example, two adjacent cells of a nucleic acid sequencing array prepared of octamers of nucleotides may have the sequences C-G-T-A-A-G-T-T and C-G-T-A-C-G-A-T. Border biopolymers may have the sequence C-G-T-A-A-C-G-T, G-T-A-A-C-G-T-A, and T-A-A-C-G-T-A-T. During the hybridization of a nucleic acid, the boundary effects will cause the border biopolymers to hybridize with segments of nucleic acid that ideally should hybridize elsewhere in the array. The presence of these boundary effects provide a level of background noise in the array and materially reduces the usefulness of the array.

It is therefore an object of the present invention to provide an improved solid-state micro-scale array of chemical products.

It is another object of the present invention to provide an array of the type described which includes preformed cells having precisely defined boundaries that separate individual cells.

It is another object of the present invention to provide a solid-state micro-scale array of oligonucleotides.

It is another object of the present invention to provide an improved method for producing solid-state micro-scale arrays of chemical products.

It is a further object of the present invention to provide a method for the photolithographic production of micro-scale arrays of chemical products.

It is yet another object of the present invention to provide an apparatus for the photolithographic production of micro-scale arrays of chemical products.

It is another object of the present invention to provide a derivatized nucleic acid monomer which has a photolabile group at the 5'-O position of the sugar.

In accordance with the present invention there is provided a solid-state micro-scale array of chemical products comprising a plurality of discrete cells defined on a surface of a substrate, each of said cells containing an individual chemical product, the cells being separated one from the other by boundaries that are precisely defined to the extent that the chemical reactivity or interactions of the product in each cell is expressible independently of and is essentially non-affected by the chemical reactivity of one or more of the products in neighboring cells. In a preferred embodiment, the chemical products in the cells are selected from the group consisting of biomonomers and biopolymers. Further, in the preferred embodiment, the individual cells of the array are substantially smaller than those heretofore achievable using physical masks. The photolithographic method described herein allows the synthesis of arrays in which individual cells occupy areas measuring only microns or tens of microns on a side. For example, an array of all 65,536 octamers of DNA, in which each octamer is contained within an area 40 microns square, will occupy a total area of about 1 cm$^2$. The present invention thus provides a method for avoiding the inadequacies of the prior art and producing arrays of very small micro-scale size with thousands of different chemical products.

In the method of the present invention, a solid-state micro-size array of chemical products is built up on a solid support, i.e., substrate, such as glass in a multi-step process. More specifically, the present method contemplates the development initially of a matrix of discrete cells on the surface of the substrate, each cell having precisely defined boundaries so that the cells are well defined, individually separated, and at identifiable locations on the substrate.

To develop such well-defined cells, the present inventors, in a preferred method, derivatize the substrate by the addition thereto of a linking group which attaches to the substrate surface and also bears a functional group, such as a hydroxyl or amino group, which is blocked by a photolabile protective group. Thereafter, a photolithographic mask having predetermined areas of transparency and opacity is positioned over the substrate and light is caused to pass through the transparent areas of the mask and fall upon those portions of the underlying layer of photolabile groups which lie beneath the areas of transparency. This action renders the photolabile groups ineffective in that they no longer protect their associated functional groups against chemical reaction with a further chemical moiety. In this step the areas of opacity are positioned over the areas of the substrate which are to become the discrete cells of the array and the areas of transparency are positioned over the areas which are to become the intervening areas of the array which separate the cells. Following the photodeprotection of functional groups in the intervening areas these same functional groups are reblocked by reaction with a reagent, e.g. acetic anhydride, which renders the functional groups inactive and in which the blocking group is substantially stable to light and chemical reagents used in the later steps of array synthesis.

These "permanently" blocked areas of the substrate surface constitute a "primary mask" which separates and defines the borders of the cells to which biomonomers and biopolymers are attached during synthesis of the array. In subsequent steps of the array synthesis, photolithographic masks are positioned such that the borders of opaque and transparent areas are positioned over areas of the primary mask of the substrate. This substantially prevents the background and boundary effects which result from the use of substrates uniformly derivatized with reactive linkers and from the use of photolithographic masks which allow contact between neighboring cells or in which the borders of the individual cells are defined by multiple masking steps. The presence of nonreactive zones between the cells of the array allows a degree of tolerance in the alignment of successive masks to be used in the later stages of array synthesis. The preparation of substrates bearing a patterned array of individual cells separated by a nonreactive primary mask may also be accomplished by other photolithographic methods. For example, the areas of the substrate which are to become the discrete cells may be protected by a photoresist layer while exposed intervening areas of substrate are coated with a primary masking layer such as a siliconizing agent. Conversely, the primary mask of a uniformly coated substrate may be etched away at the sites of the discrete cells while the intervening border areas are protected by a photoresist layer.

At the completion of the substrate preparation each cell in the array contains linkers terminating in functional groups blocked with photolabile moieties as described above. Thereafter, a second photolithographic mask having predetermined areas of transparency and predetermined areas of opacity is positioned over the entire substrate and light is caused to pass through the transparent areas of the photolithographic mask and fall upon selected cells which lie beneath the areas of transparency, resulting in the photodeprotection of the functional groups in the exposed cells.

Once the functional groups in the selected cells are deprotected, the surface of the substrate is flooded with a selected chemical moiety, for example, a solution containing one of the nucleotides of DNA in a form suitable for solid-phase synthesis, such as the beta-cyanoethylphosphoramidite, these nucleotides also having associated therewith a photolabile group, for example blocking the 5'-O position. The nucleotides attach themselves to the exposed functional groups, for example hydroxyls, and become anchored in individual cells on the substrate.

Thereafter, a further photolithographic mask is positioned over the substrate, this further photolithographic mask generally having selected areas of transparency and selected areas of opacity that are of a different pattern than the pattern of transparent and opaque areas of the previous photolithographic mask. Light is directed through the transparent areas of this further photolithographic mask onto the substrate surface. Generally, the pattern of transparency and opacity of this further photolithographic mask is selected to exclude light from all or part of those cells which received the first nucleotide and to deprotect other of the cells that contain functional groups. Following this deprotection step, the substrate is flooded with solution containing a second nucleotide having a photolabile group associated therewith, for example, which attaches itself to those functional groups or nucleotides which were exposed by the most recent light treatment through the further mask.

The foregoing steps of masking the substrate, exposing the substrate to light in selected areas to deprotect such areas, addition of a further chemical moiety having a photolabile group associated therewith to those cells which have been exposed by the most recent light treatment, etc., are repeated for that number of times required to build up within each cell whatever specific chemical product is desired, for example a biopolymer comprising the nucleic acid sequence of GACT, AACT, etc. Each cycle of nucleotide addition may include additional steps, e.g., oxidation of phosphite to phosphate, as required by the particular synthesis chemistry used. Modified bases, as well as modified sugars and internucleotide phosphate linkages may also be incorporated into members of the array if desired; for example, to test the effect of specific modifications on hybridization or for increased stability of array members.

The present invention thus provides a photolithographic method for the parallel synthesis of multiple chemical products disposed individually at specific predetermined positions of an array on a surface of a substrate. The general method comprises, first, derivatizing the surface of the substrate with a functional group for the attachment of a chemical moiety. The functional group may include a "linker" to space the reactive site away from the surface of the substrate. The functional group is derivatized with a photolabile protective group or with a chemical moiety having a further functional site which is blocked by a photolabile protective group. Next, first selected areas of the surface of the substrate are illuminated with light of a wavelength and intensity and for a sufficient amount of time to deprotect the one other functional sites at the selected areas without deprotecting the functional sites not at the selected areas. Subsequently, the substrate is treated with a chemical moiety having a first functional site capable of reacting with and attaching to the photodeprotected site of the functional group while substantially not attaching to other sites on the substrate. Further, the chemical moiety has at least a second functional site which is blocked by a photolabile protective group. The moiety is different from or the same as the functional group. Subsequently, second selected areas of the surface of the substrate are illuminated with light of a wavelength and intensity and for a sufficient amount of time to deprotect the functional sites at the second selected areas without deprotecting other functional sites not at the selected areas. The second selected areas are different from or the same as the first selected areas. The steps of treating with chemical moieties and illuminating selected areas are repeated, wherein the chemical moieties are different from or the same as the functional group chemical moiety and wherein the selected areas are different from or the same as the first and second selected areas. Thus, an array of the desired multiple chemical products is synthesized and each individual chemical product is located at a specific predetermined position in the array.

In a preferred embodiment of the present invention, the chemical moieties comprise nucleotide derivatives bearing a photolabile protecting group on the 5'-oxygen and the chemical products comprise oligonucleotides. A number of photolabile hydroxyl-protecting groups are available for this purpose, including 2-nitrobenzyl, 6-nitroveratryl, 2-nitrobenzyloxycarbonyl, 6-nitroveratryloxycarbonyl, and analogs having comparable chemical and photochemical properties. The preferred substrate for the synthesis of oligonucleotide arrays is one functionalized with hydroxyl groups. Where the chemical products comprise peptides, the preferred chemical moieties comprise amino acid derivatives bearing a photolabile protective group on the amino function. A number of photolabile blocking groups are also available for the amino function, including the 2-nitrobenzyloxycarbonyl, 6-nitroveratryloxycarbonyl, 3,5-dimethoxybenzyloxycarbonyl, alpha,alpha-dimethyl-3,5-dimethoxybenzyloxylcarbonyl, various arenesulphonyl groups, and analogs having comparable chemical and photochemical properties. The preferred substrate for the synthesis of peptide arrays is one functionalized with amino groups.

The illumination of the selected areas is carried out, in a preferred embodiment, by illuminating the substrate through a photolithographic mask or by illuminating the selected areas with a laser or focused beam of light. The substrate in a preferred embodiment is a plate of a material selected from the group consisting of soda-lime glass, borosilicate glass, quartz, or silicon.

The present invention also provides for a method for the parallel synthesis of multiple chemical products disposed individually at specific predetermined positions in discrete cells of an array on a surface of a substrate. The discrete cells of the array are separated one from another by border areas. The method comprises preparing the surface of the substrate by derivatizing the surface with a functional group for the attachment of a chemical moiety. The functional group may include a linker to space the reactive site away from the surface of the substrate. The functional group is derivatized with a photolabile protective group or with a chemical moiety having a further functional site which is blocked by a photolabile protective group. First selected areas of the surface of the substrate are illuminated with light of a wavelength and intensity and for a sufficient amount of time to deprotect the functional sites at the selected areas without deprotecting the functional sites not at the selected areas. The first selected areas substantially correspond to the border areas separating the discrete cells of the array. The substrate is then treated with a chemical agent capable of reacting with and attaching to the photodeprotected sites at the selected areas while substantially not reacting with other sites on the substrate. Examples of such chemical agents include acylating agents, such as acetic anhydride, for reaction with hydroxyl and amino functions. The resulting blocked functional sites are substantially non-reactive and non-photolabile. Next, second selected areas of the surface of the substrate are illuminated with light of a wavelength and intensity and for a sufficient amount of time to deprotect the functional sites at the second selected areas without deprotecting other functional sites not at the selected areas. The second selected areas correspond to at least one of the discrete cells of the array. Then the substrate is treated with a chemical moiety having a first functional site capable of reacting with and attaching to the deprotected site of the linker or functional group while substantially not attaching to other sites on the substrate. The third chemical moiety has at least a second functional site which is blocked by a photolabile protective group. The moiety different from or the same as the functional group. Third selected areas of the surface of the substrate are then illuminated with light of a wavelength and intensity and for a sufficient amount of time to deprotect the functional sites of those linkers or chemical moieties having photolabile protecting groups at the selected areas without deprotecting other functional sites not at the selected areas. The third selected areas correspond to at least one discrete cell of the array. The third selected areas are different from or the same as the second selected areas. The steps of treating with chemical moieties and illuminating selected areas are then repeated a sufficient number of times to produce the desired array of chemical products. During the repeated treatment steps, the chemical moieties are different from or the same as the chemical moieties. Also, the selected areas are different from or the same as the previous selected areas. Thus, an array of the desired multiple chemical products is synthesized and each individual chemical product is located in a discrete cell at a specific predetermined position in the array.

The synthesis of many different products may thus be carried out in parallel in the different cells of the array with the product contained in each cell being determined by the pattern of masking and addition steps. The present invention is therefore particularly useful in providing micro-scale arrays of biopolymer sequences, such as oligonucleotides and peptides having a large number of members and capable of being synthesized on solid supports from monomers. The photolithographic method of parallel synthesis may also, of course, be carried out in the absence of a "primary mask", though with certain of the boundary effects mentioned above.

Upon completion of the masking and addition steps, the entire array is subjected to light and/or other treatments as necessary, e.g., ammonium hydroxide, to deprotect all of the chemical products in the several cells without cleaving the products themselves from the support. The entire array may then be exposed to a solution containing molecules which interact with specific members of the array, causing those members to become associated with detectable reporter groups, such as fluorescent moieties or radioisotopes. Inasmuch as the identity of such substrate member may be determined from its position in the array, these interactions may be used to identify specific properties of the solute and/or substrate molecules. For example, exposure of an array of oligonucleotides to a solution of labeled DNA or RNA under conditions which allow hybridization of substrate members to complementary sequences in the labeled molecules may be used to simultaneously identify many such sequences in the labeled molecules. Oligonucleotide arrays produced by the methods of the present invention therefore have many applications to DNA mapping, sequencing, fingerprinting and diagnostics.

Photolithographic masks are easily prepared and positioned with great precision. Therefore, the method of the present invention makes the production of micro-scale arrays of biopolymers, such as octamers of DNA, a relatively direct process.

A laser or focused light beam might also be used to deliver light to specific locations in the array for photodeprotection. Light beams may be accurately and repeatably directed onto the substrate of a micro-scale array by one of a number of methods. For example, a confocal scanning microscope would move the sample while holding the focused beam steady while a laser scanning microscope uses lenses and mirrors to accurately direct a laser beam over a substantially stationary sample.

The photolabile groups used in the present invention are well known in the art (Pillai, in Organic Photochemistry, Vol. 9, A Padwa, ed., Marcel Dekker, Inc., New York, 1987, pp. 225–323). The 2-nitrobenzyl and related groups have been used to protect hydroxyl function. Notably, the 2-nitrobenzyl group has been used to protect the 2'-hydroxyl of ribonucleotides during oligoribonucleotide synthesis; efficient removal of the protective function from the synthesized oligomers has been accomplished by exposure in solution to ultraviolet light of a wavelength greater than 320 nm, without damage to the nucleoside bases. The 6-nitroveratryl group (i.e., 4,5-dimethoxy-2-nitrobenzyl) has been used as a photolabile protective group for the hydroxyl function in synthetic carbohydrate chemistry and was efficiently removed by irradiation at wavelengths greater than 320 nm. Additional photocleavable protective groups for the hydroxyl function include the 2-nitrobenzyloxycarbonyl and related groups. Analogs of these groups which neither substantially affect the reactivity of the blocking group nor substantially affect the photolability of the blocking group are also acceptable for use as photolabile blocking groups.

The 2-nitrobenzyloxycarbonyl, 6-nitroveratryloxycarbonyl, 3,5-dimethoxybenzyloxycarbonyl, alpha, alpha-dimethyl-3,5-dimethoxylbenzyloxycarbonyl and arenesulphonyl groups have all been used as photolabile protecting groups for the amino-terminus during peptide synthesis. These groups are generally removed by irradiation with light of wavelength greater than about 320 nm. Photolabile blocking or photoactivating groups are also known for other functions, including the carboxyl, thiol and carbonyl groups and photolytic deprotection or photoactivation reactions have been employed in the synthesis of a variety of chemical products.

In the preferred method of the present invention photolabile blocking groups are used in place of the normal terminal blocking groups used in solid-phase synthesis, which are removed by chemical treatments. Thus, for example, the 5'-O'-dimethoxytrityl group normally used in oligonucleotide synthesis is replaced by a photosensitive hydroxyl-protecting function and the tertiary-butoxycarbonyl function used to protect the amino function in solid-phase peptide synthesis is replaced by a photolabile amine-protecting group. This principal may be extended to the solid-phase synthesis of other types of polymers, such as oligosaccharides, in which the subunits bearing a terminal blocking group are incorporated stepwise onto the support. More generally, the combination of photolithographic methods with chemical syntheses employing photolabile blocking or photoactivating groups may be used to prepare arrays of molecular variants of a variety of chemical products on solid supports.

The present invention provides for an apparatus for the photolithographic production of a solid-state micro-scale array of selected biomonomers and biopolymers. The apparatus comprises a base member including at least one generally open concave cavity, and at least one aperture through the base member into the cavity. There is also a substrate member having a length and width being such as to at least completely cover the open cavity in the base member, and being treated such that the substrate member has photolabile protected functional groups available in cells of an array along at least one surface of the substrate member. The substrate member consists of soda-lime glass, borosilicate glass (e.g., PYREX, Dow Corning) or other material, such as quartz or silicon, which is substantially transparent to the wavelengths of light used to remove the photolabile blocking groups employed in the oligomer synthesis. The functional groups are reactive with the selected biomonomers when the functional groups are deprotected. A set of photolithographic masks is provided, each of which hag different transparent portions and different opaque portions. Further, there is a source of light of a wavelength and intensity sufficient to labilize a photolabile chemical group. The apparatus operates such that the transparent substrate member is joined to the base member, wherein the cavity and the substrate member form a reaction chamber. One of the photolithographic masks is placed between the substrate member and the source of light. The transparent portions of the mask substantially correspond to those cells of the array where the selected biomonomer is to be added to the array. The source of light is operated to labilize the photoprotecting groups exposed to the light resulting in the cells of the array having exposed reactive groups. The labilized groups are rinsed from the reaction chamber via the aperture in the base member. The reaction chamber is supplied with a solution, again via the aperture, which includes a selected photolabile protected biomonomer which is reactive to the exposed reactive groups available in the cells of the array along the one side of the substrate member. The biomonomer reacts with the linking group and forms a layer of photolabile protected groups in the array. A different photolithographic mask is placed between the substrate member and the source of light, the source of light is again operated, and the reaction chamber is again supplied with a solution including a selected photolabile protected biomonomer which is reactive to the exposed reactive groups available in the cells of the array along the one side of the substrate member. The process is repeated until the desired micro-scale array is produced.

The present invention also provides for a nucleoside comprising a saccharide selected from the group consisting of ribose and deoxyribose. Further, there is a base component selected from the group consisting of purines and pyrimidines attached to the saccharide at the 1'-position of the saccharide. In addition, there is a photolabile protecting group at the 5'-position of the saccharide. In a preferred embodiment of the invention, the purine or pyrimidine is selected from the group consisting of adenine, cytosine, guanine, thymine, uracil, and derivatives thereof.

The present invention may be better understood by reference to the following detailed description of exemplary embodiments when considered in conjunction with the drawings in which:

BRIEF DESCRIPTION OF THE DRAWINGS

FIGS. 3-1, 3-2, and 3-3 are is diagrams illustrating the generation of a micro-scale solid-state array of biopolymers according to one embodiment of the present invention;

FIGS. 4-1, 4-2, 4-3, and 4-4 are is diagrams illustrating the generation of a micro-scale solid-state array of biopolymers according to another embodiment the present invention;

Deoxyribonucleoside derivatives in which the 5'-hydroxyl is protected as a photosensitive carbonate ester are readily prepared by reaction of 2-nitrobenzyloxycarbonyl chloride and related compounds such as 6-nitroveratryloxycarbonyl chloride with thyroidine or the N-protected derivatives of deoxyadenosine, deoxycytidine and deoxyguanosine. The chloroformates react preferentially at the primary hydroxyl group of the nucleoside. Analogously, the corresponding 5'-carbonate esters are prepared from N-protected ribonucleoside derivatives in which the 2'-hydroxyl is also blocked, e.g. as a silyl ether.

Figure 1:
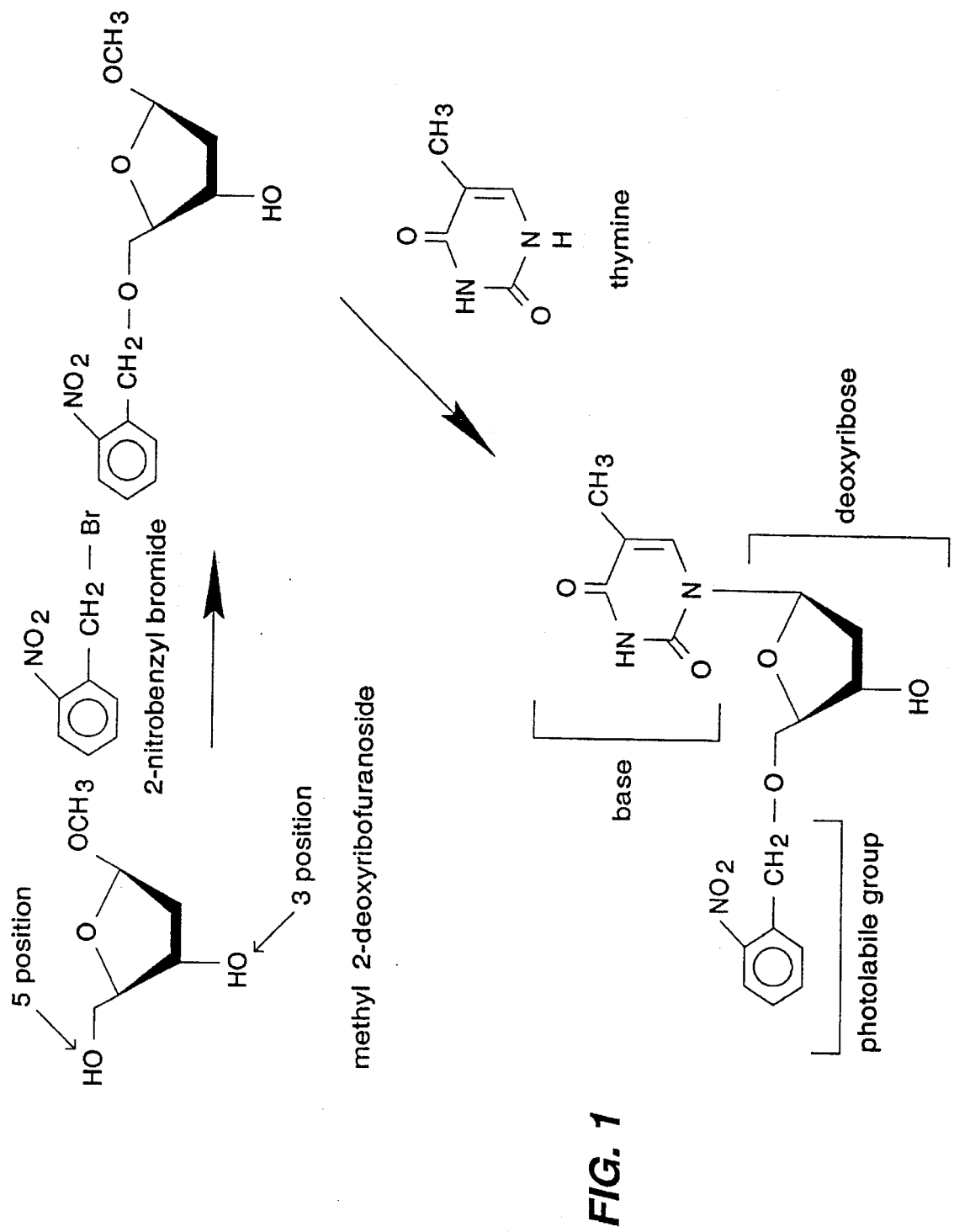
FIG. 1 is a schematic diagram of the preparation of a deoxyribonucleic acid base with a photolabile group in the 5'-position for use in the present invention.

Nucleosides in which the 5'-hydroxyl is protected as a photocleavable ether are prepared by reaction of the primary hydroxyl with 2-nitrobenzyl bromide or 6-nitroveratryl bromide in the presence of sodium hydride. In the case of nucleosides in which the purine or pyrimidine is substantially reactive (e.g., thymine and guanine) leading to undesired products, a multistep synthesis is used as indicated in FIG. 1. Initially, the unsubstituted sugar is reacted with the photolabile protecting reagent, and the resulting protected sugar is then reacted (after conversion to its corresponding pentosyl chloride) with the appropriate purine or pyrimidine derivative, via published glycosylation procedures, to give the 5'-O-protected nucleoside. The glycosylation procedure includes the initial steps of protecting the 3-hydroxyl and converting the sugar to a 1-chloro derivative, not shown. In the case of ribonucleoside the 2- and 3-hydroxyls of the unsubstituted sugar are initially protected as the isopropylidene derivative.

The 5'-O-protected nucleoside derivatives are then converted to 3'-O derivatives such as the phosphoramidites or H-phosphonates by standard procedures for use in solid-phase oligonucleotide synthesis.

Figure 2:
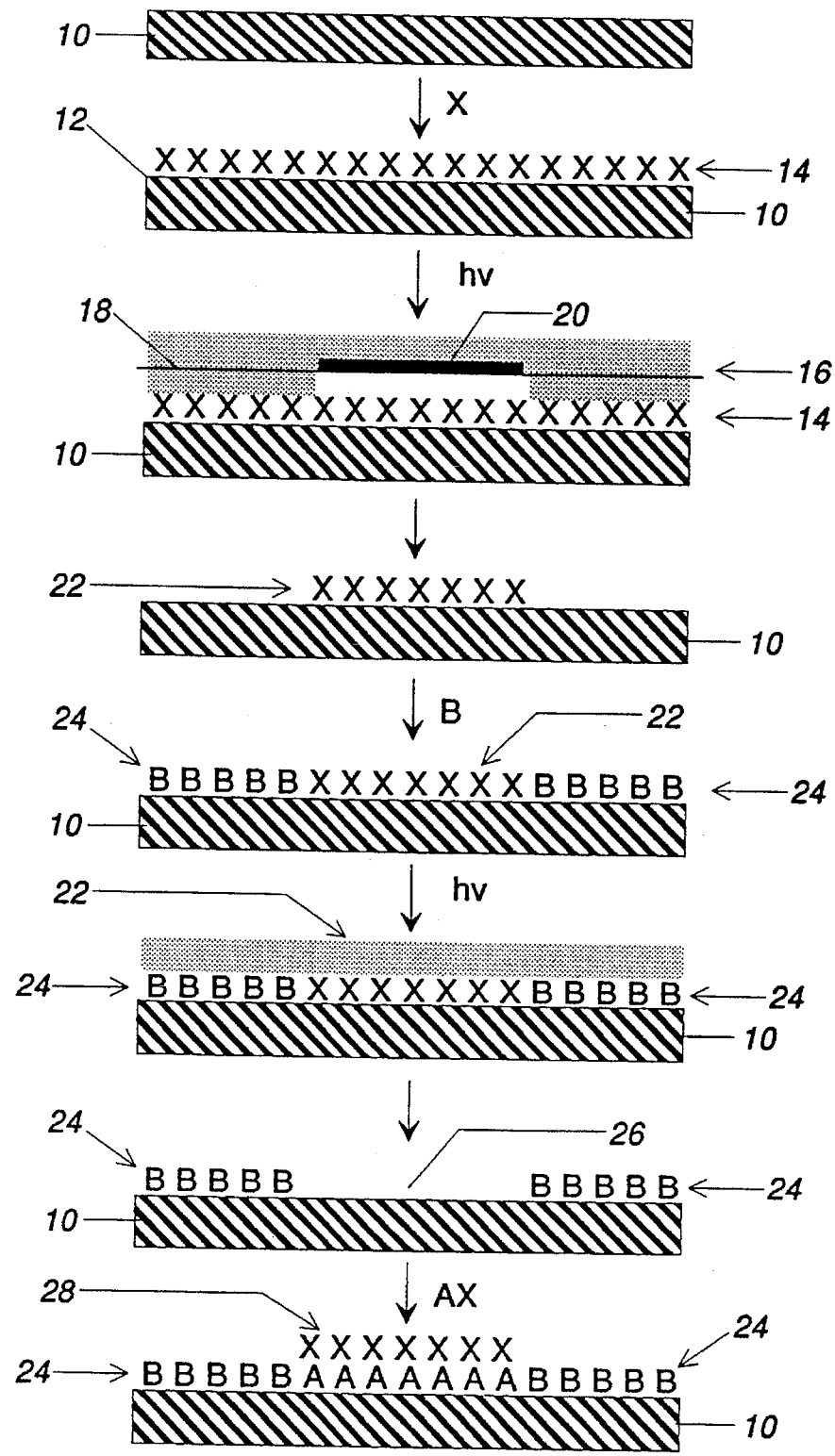
FIG. 2 is a diagram depicting a preferred embodiment of the present invention wherein a primary mask is chemically attached to the surface of a substrate.
Figure 3A:
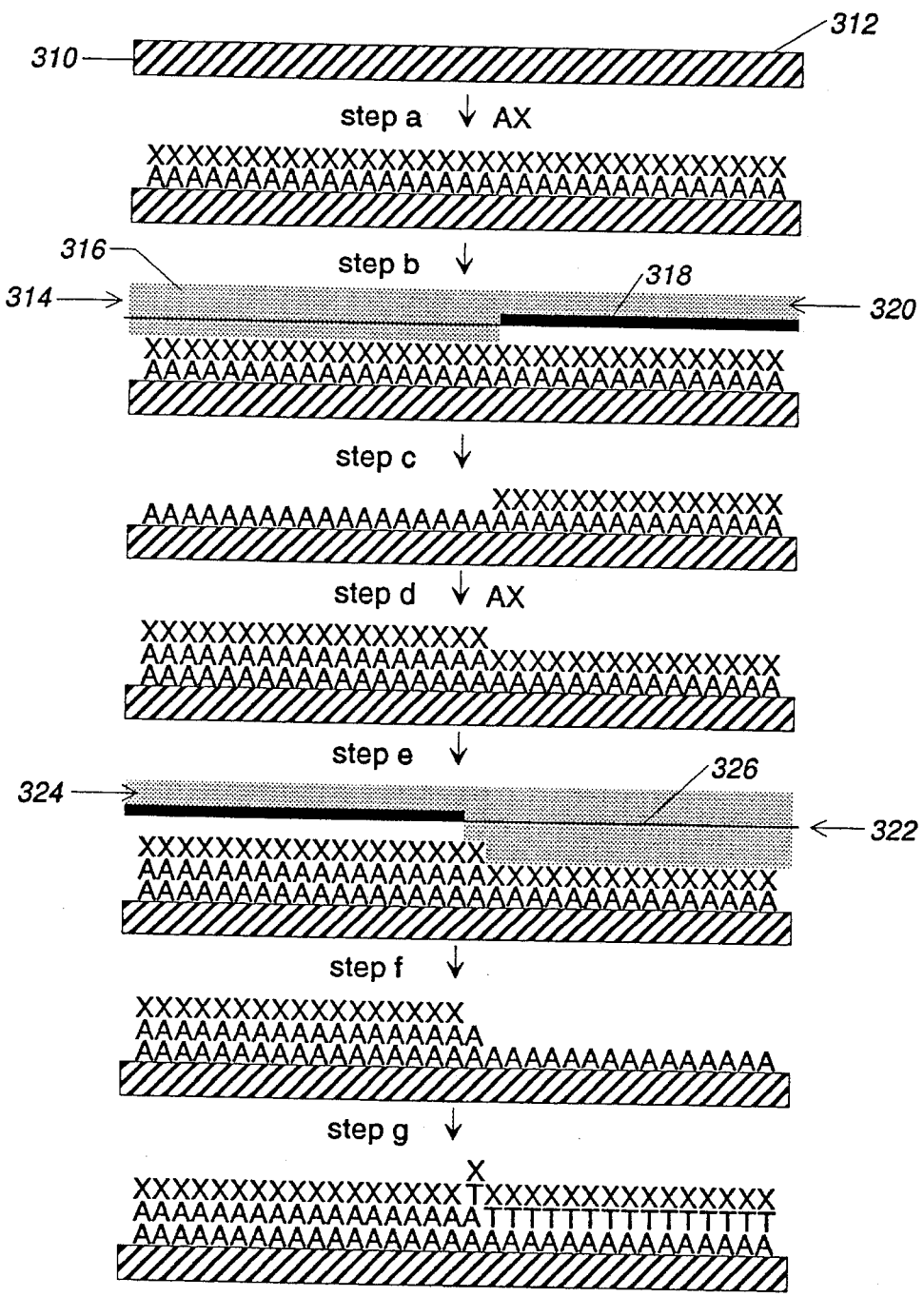
Figure 3B:
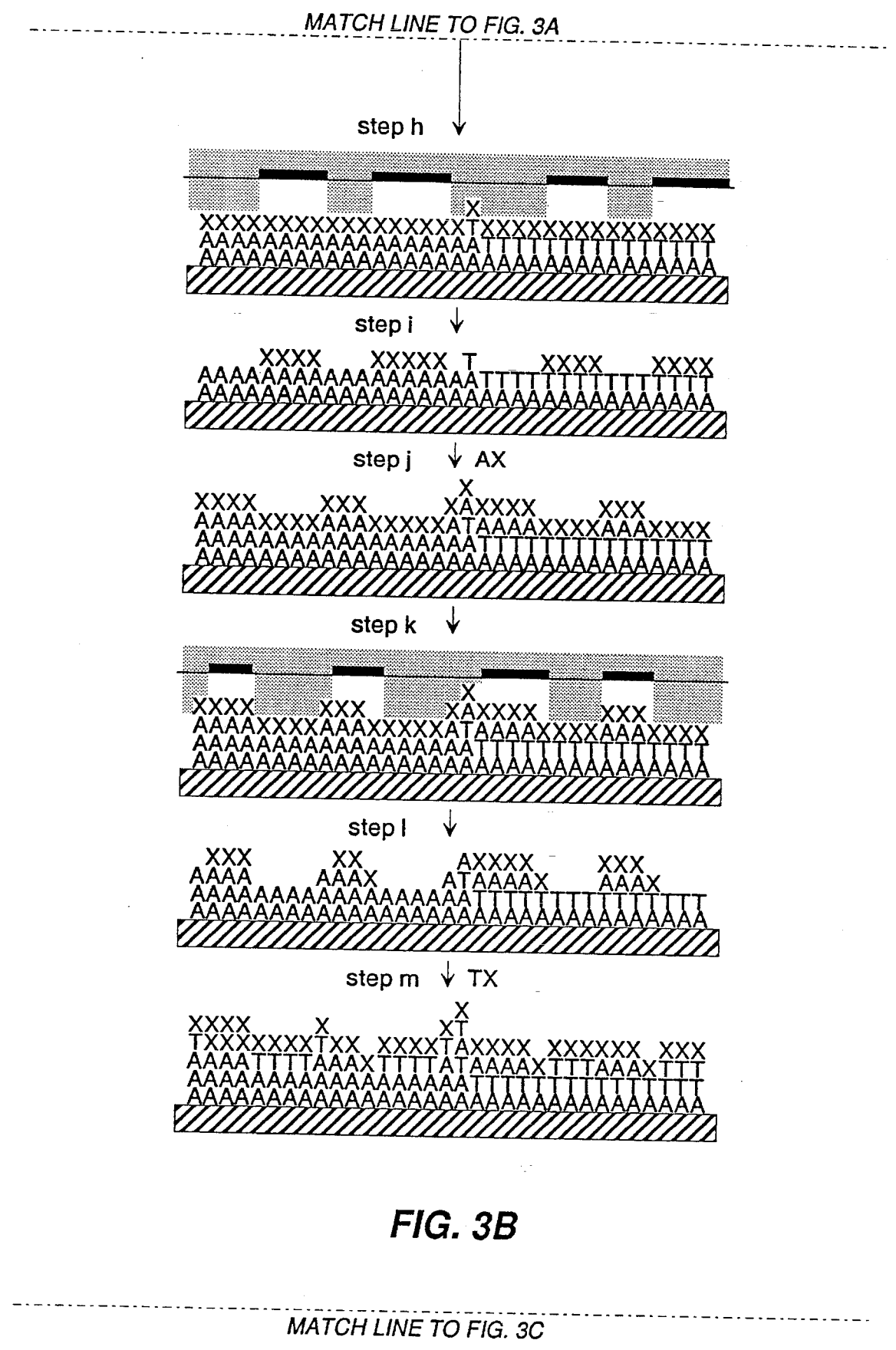
Figure 3C:
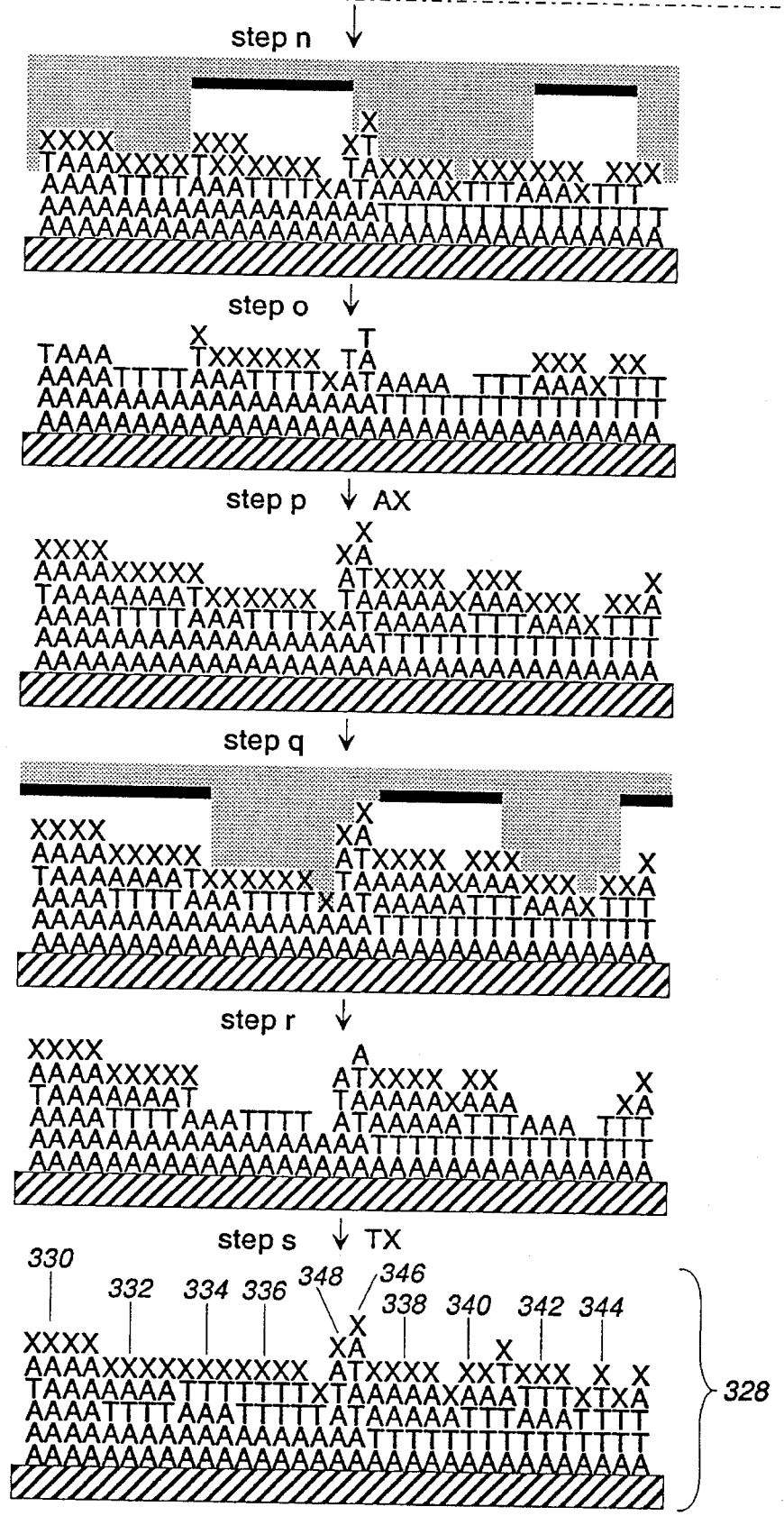
Figure 4A:
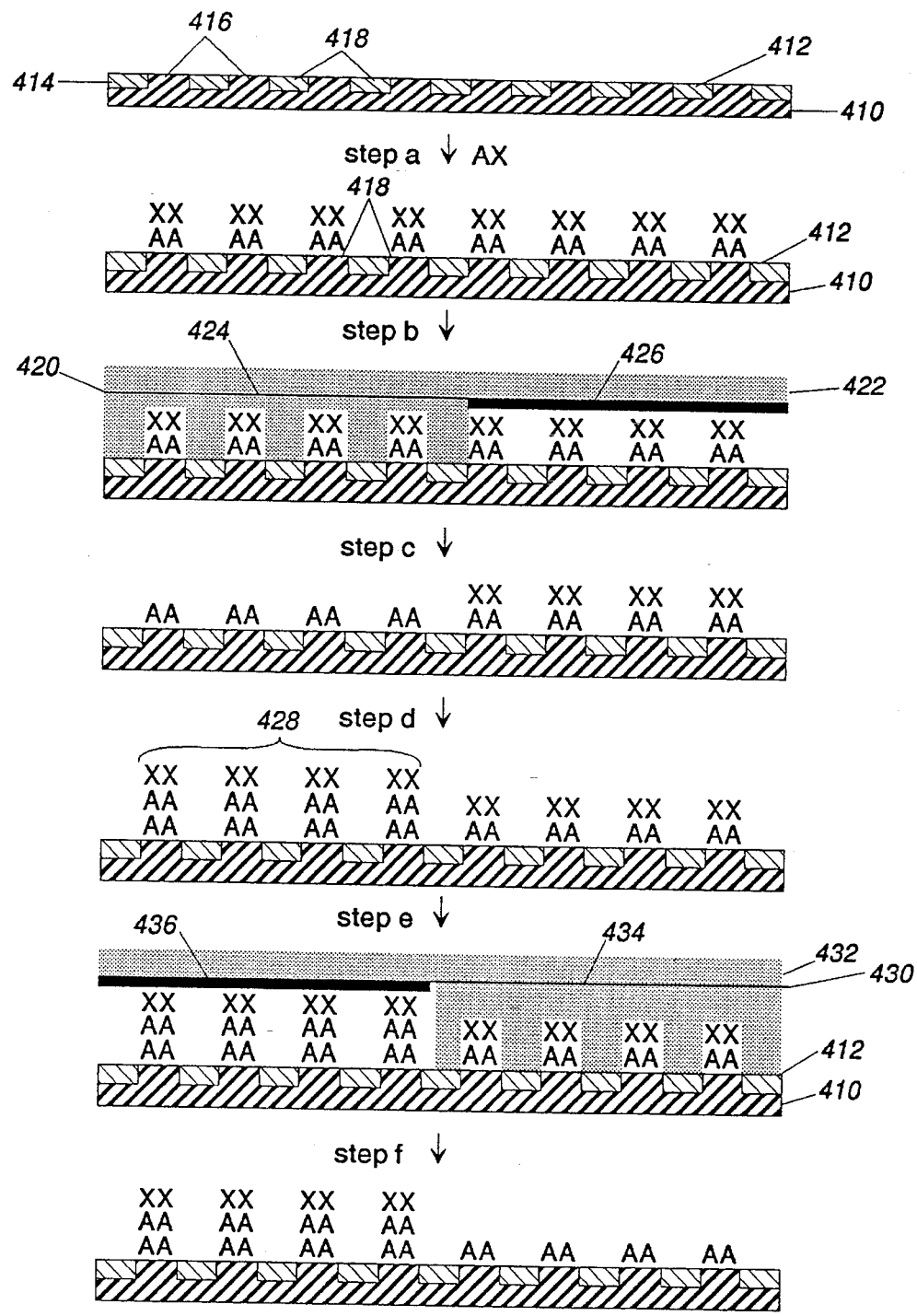
Figure 4B:
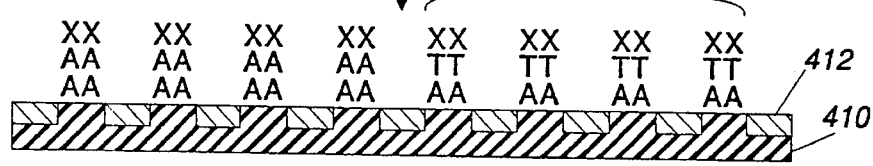
Figure 4B:
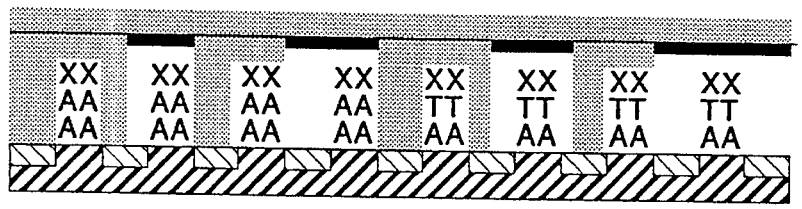
Figure 4B:
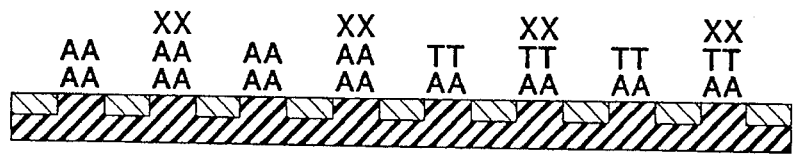
Figure 4B:
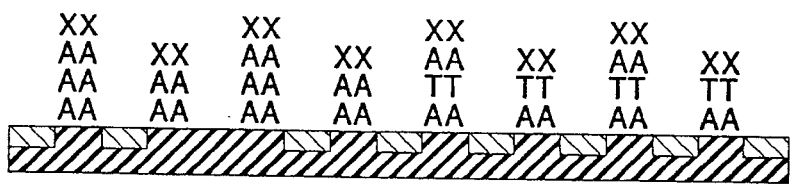
Figure 4B:
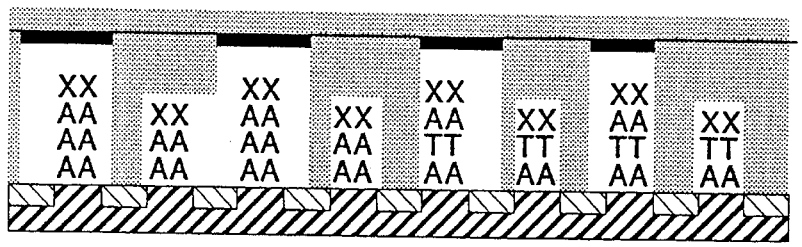
Figure 4C:
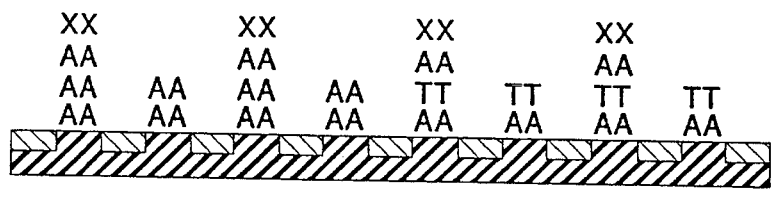
Figure 4C:
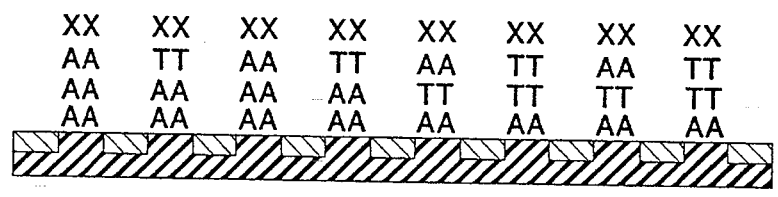
Figure 4C:
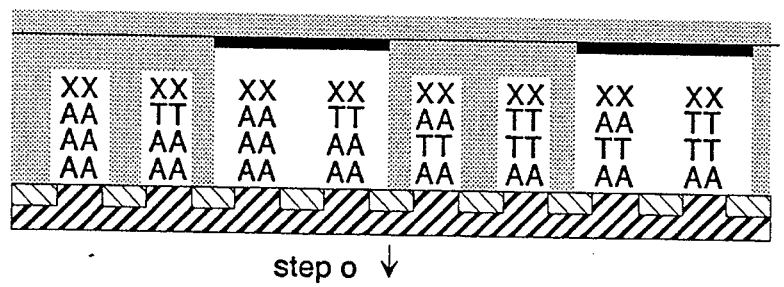
Figure 4C:
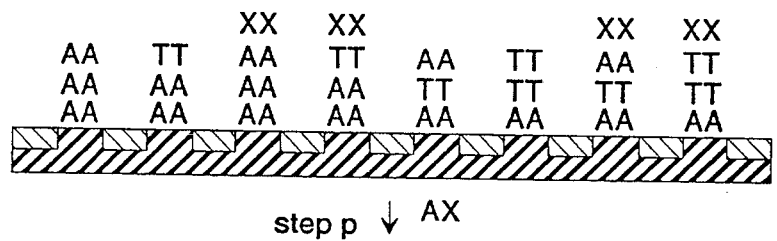
Figure 4C:
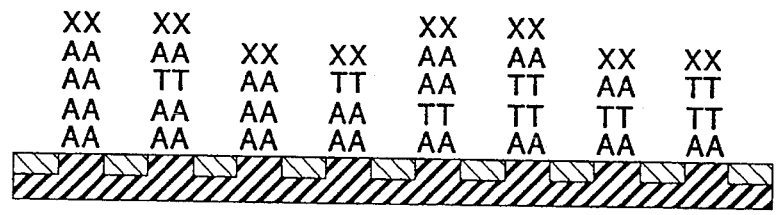
Figure 4D:
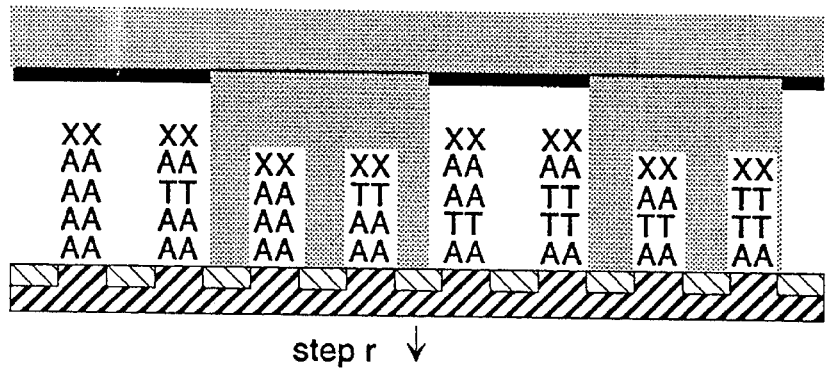
Figure 4D:
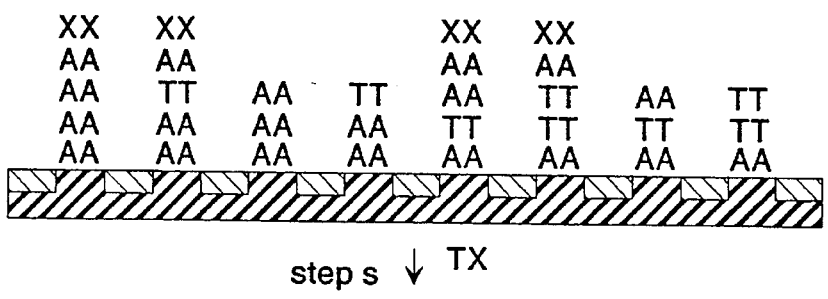
Figure 4D:
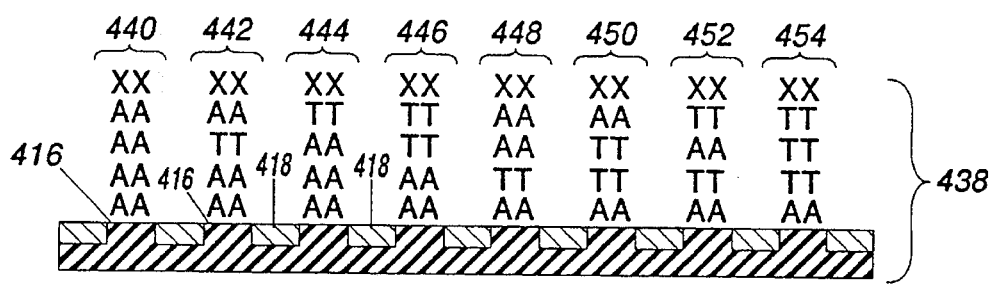

Referring now to the drawings in which like reference characters designate like or corresponding parts throughout the Figures, there is shown in FIG. 2 a substrate 10. For purposes of clarity in explaining the present invention, the following description refers to an array of biopolymers, i.e., sequences of nucleic acids, built up from biomonomers, i.e., individual nucleic acids, and specifically to sequences of the four DNA nucleotides of guanine (G), adenine (A), thymine (T) and cytosine (C). This description could just as easily refer to an array of different biopolymers (such as RNA, peptides, or oligosaccharides) built up from different biomonomers (such as the RNA nucleotides, amino acids or saccharides). A suitable material for such a substrate 10 would be a plate of soda-lime glass, borosilicate glass or quartz. The substrate 10 has been previously prepared to be reactive to a photolabile group, X, or to a moiety bearing a functional group blocked by X, as well as various biomonomers, represented here as AX, and a blocking group, represented by B. The substrate 10 is treated with a photolabile group, X, or the aforesaid moiety bearing X, which reacts with the functional groups on the surface 12 of the substrate 10 to form a layer 14 on the substrate 10. A photolithographic mask 16, with transparent regions 18 and an opaque region 20, is placed between the layer 14 and a source of light, not shown. Light from the source of light penetrates the transparent regions 18 to strike a portion of the layer 14. The protecting groups are labilized from those exposed portions of the layer 14 and the labilized groups are removed leaving a remaining protected portion 22 of the layer 14. The substrate 10 is treated with a non-photolabile blocking group, B, which reacts with the functional groups on the surface 12 of the substrate 10 to form layers 24 on the substrate 10. The layers 24 act as non-reactive non-photolabile boundary areas between the cells of the array. The substrate 10 is then illuminated with the light source to labilize the remains of the layer 14. The protecting groups are removed leaving an exposed cell area 26 which is reactive toward the selected biomonomer with a photolabile group, AX. The substrate 10 is next treated with the selected biomonomer, AX, which attaches to the substrate 10 in the area 28. Thus, selected biomonomers may be added to the cells of the micro-scale array without attachment to the boundaries between the cells, as shown for the equivalent array illustrated by FIGS. 4-1, 4-2, 4-3, and 4-4.

FIGS. 3-1, 3-2, and 3-3 are diagrams illustrating the generation of a micro-scale solid-state array of biopolymers according to one embodiment of the present invention. A substrate 310 has a surface 312 for attaching biomonomers. In the first step, a, of the generation of the array, a biomonomer, represented in this case by A, with a photolabile protecting group, represented in this case by X, is attached to the surface 312 of the substrate 310. This produces a carpet of protected biomonomers attached to the surface. A mask 314 with transparent areas 316 and opaque areas 318 is placed over the substrate and biomonomers in step b. Light 320 is projected on to the mask and through the transparent areas 316. The light 320 penetrates through the transparent areas 316 onto a portion of the photolabile groups attached to the biomonomers. The photolabile groups, X, which have been illuminated by the light 320 are removed from the biomonomers in step c. In step d, the substrate is then treated with another biomonomer with a photolabile protecting group, AX. Another mask 322 is placed over the array and light 324 is projected on to the mask 322 in step e. The light 324 penetrates the transparent area 326 of the mask 322. In step f, those photolabile groups, X, which were illuminated by the light 324 are removed. The matrix is then treated with another biomonomer with a photolabile protecting group, TX, in step g. The process of masking, illumination, and treatment with biomonomers with photolabile protective groups is repeated a number of times in steps h through s, to produce the final array 328. The array 328 contains a series of different biopolymers which occupy the positions of the elements of the array 328. The elements illustrated in the final array 328 of FIG. 3 represent eight different polynucleotide sequences where A represents adenine and T represents thymine. The sites of the final array 328 are 330 for the sequence AAA; 332 for the sequence AATA, 334 for the sequence AAAT; 336 for the sequence AATT, 338 for the sequence ATAA; 340 for the sequence ATTA; 342 for the sequence ATAT; and 344 for the sequence ATTT. An example of the boundary effect is demonstrated by the sequences AATATAT 346 and AAATT 348 which have been formed by misalignments of the masks, in steps b, e, h, k, n, and q, during the formation of the final array 328. The sequences 346 and 348 are situated between the elements 336 and 338. In a hypothetical experiment, if the final array 328 was treated with tetrameric nucleic acids, several of the tetrameters hybridizing with the sequence 346 would have no relationship to the sequence 336 or the sequence 338. For example, a sequence complementary to the sequence ATAT, represented at the site 342, would bind at the upper end of the sequence 346. In a similar way, a nucleic acid sequence the sequence AATA, the same sequence as is seen at site 332, would hybridize with the lower portion of the sequence 346. Therefore, the presence of sequences similar to the sequence 346 or the sequence 348 contribute to noise in the background of the final array 328. (These hypothetical examples of hybridization are given for illustrative purposes only; in practice, arrays of longer oligonucleotides are used.)

FIGS. 4-1, 4-2, 4-3, and 4-4 are diagrams illustrating the generation of a micro-scale solid-state array of biopolymers according to another embodiment of the present invention. A substrate 410 has a surface 412 which has a primary mask 414. The primary mask 414 divides the surface 412 into areas 416 to which biomonomers are capable of being attached and areas 418 to which biomonomers cannot attach. When the surface 412 of the substrate 410 is flooded in step a with a biomonomer having an attached photolabile protecting group (AX) the biomonomer attaches only in those areas 416 where they are capable of attaching. In step b, a secondary mask 420 is placed over the surface 412 of the substrate. Light 422 is projected on to the photolithographic mask 420. The light penetrates the transparent portion 414 of the mask and is blocked by the opaque 426 of the mask 420. Only those photolabile groups in the cells 416 of the substrate 410 exposed to the light 422 are deprotected in step c. The substrate 410 is then treated with additional biomonomer having a photolabile protecting group (AX) which forms the first set of biopolymers 428 in step d. In step e, a second photolithographic mask 430 is placed over the substrate 410 and light 432 is projected on to the surface 412 of the substrate 410 through the transparent areas 434 of the photolithographic mask 430. The light 432 is blocked by the opaque areas 436 of the photolithographic mask 430. In steps f and g, the exposed photolabile groups are removed and the substrate 410 is then treated with another biomonomer having a photolabile protecting group (TX) which forms a second set of biopolymers 438. The process of masking, projecting of light, and treatment with protected biomonomers is repeated several times, in steps h through s until the desired array is produced. The final array 438 contains eight different sets of biopolymers 440, 442, 444, 446, 448, 450, 452, and 454. These sets of biopolymers exist in discrete cells 416. In the array of the present invention, there are none of the boundary effects as are seen in an array prepared according to the previous embodiment. When an oligonucleotide array of the present invention is treated with nucleic acid sequences, hybridization may occur only at the discrete sites 416 and not in the boundary regions bordering each cell 418.

Figure 5:
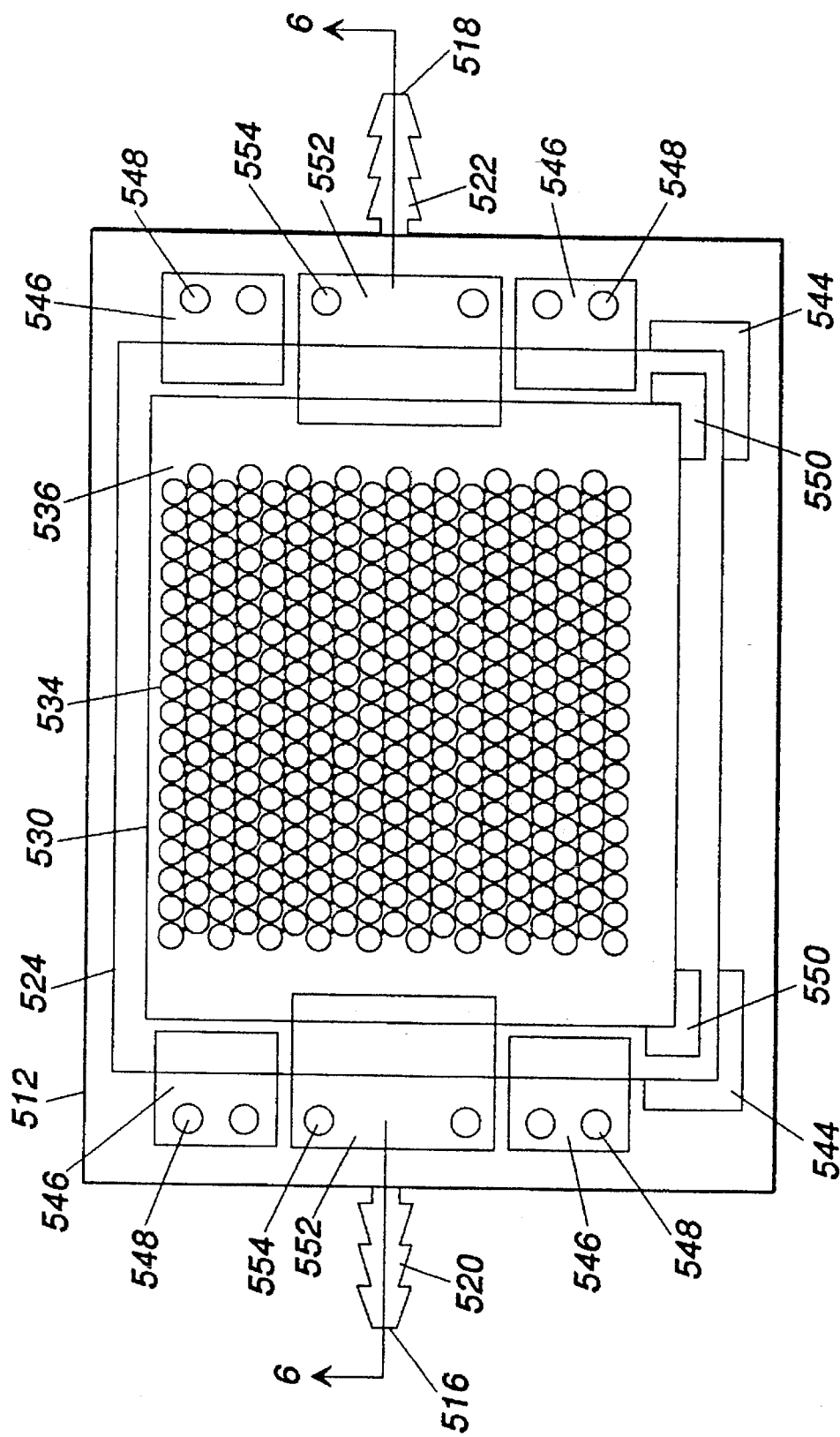
FIG. 5 is a perspective view of a flow cell to be used in producing micro-scale arrays of the present invention.
Figure 6:
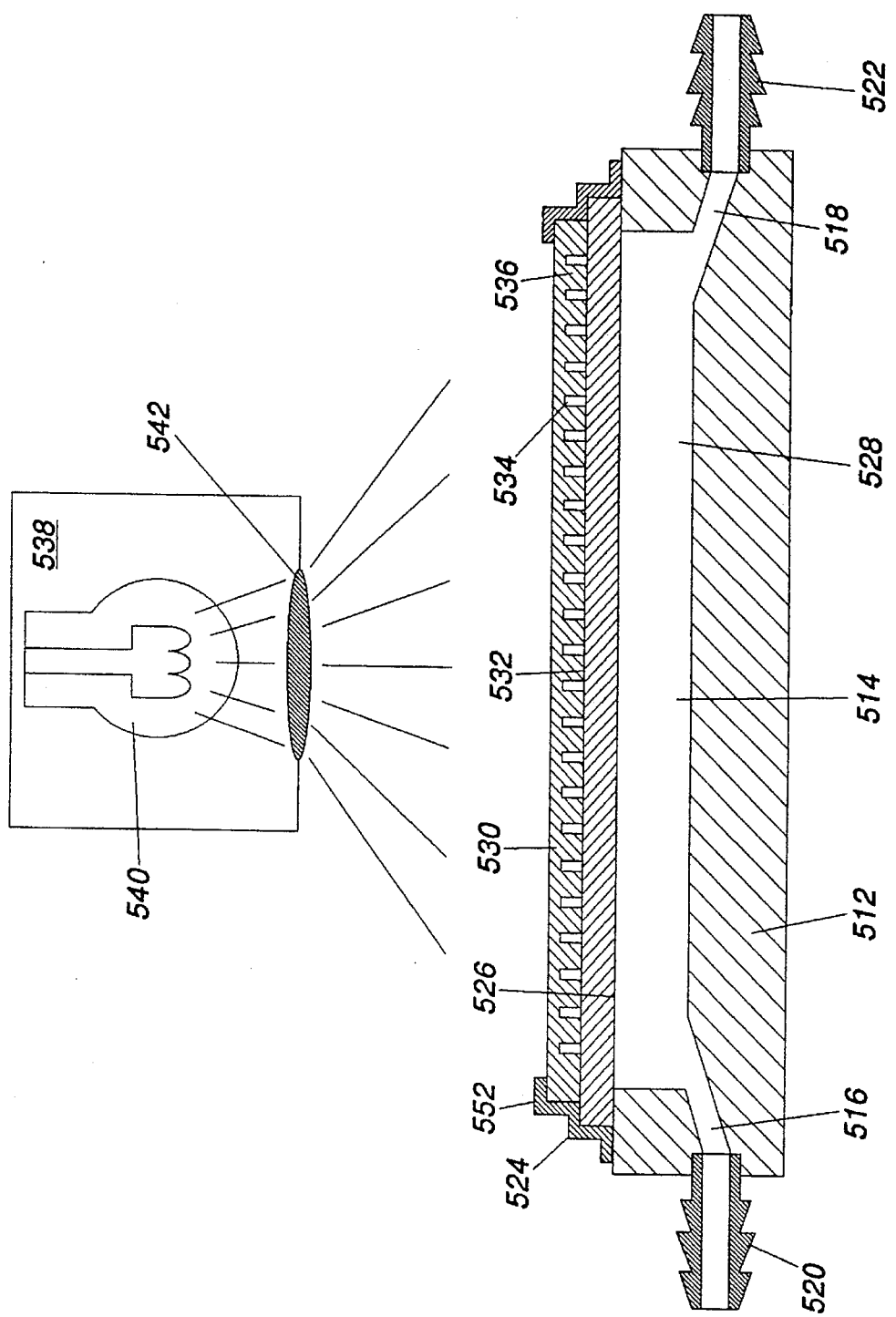
FIG. 6 is a cross-sectional diagram of the flow cell of FIG. 8 taken through 6—6.

A top view of a flow cell 510 for preparing solid-state micro-scale arrays is shown in FIG. 5; a cross-sectional view of the flow cell 510 is shown in FIG. 6. The flow cell 510 comprises a base member 512 having a concave cavity 514 formed, milled or otherwise structured into the base member 512. The base member 512 is preferably constructed of a generally non-chemically reactive polymeric material such as TEFLON (DuPont) although other nonreactive materials such as siliconized glass, may be used. Two apertures 516 and 518 through the base member 512 provide direct connection between the cavity 514 and the exterior of the base member 512. The apertures 516 and 518 are in direct communication with connectors 520 and 522, respectively. The connectors 520 and 522 are adapted for connection with tubing for the delivery or removal of liquid materials to and from the cavity 514.

A substrate member 524 is placed on the base member 512. A gasket of non-reactive material, such as TEFLON (DuPont), may be used as a seal between the two members 524 and 512. The substrate member 524 has a length and width such that it completely covers the open cavity 514. Thus, the cavity 514 and one side 526 of the substrate member 524 form a reaction chamber 528. The substrate member 524 preferably comprises a soda-lime glass, borosilicate glass or quartz plate, but any suitable material, which is transparent to the wavelengths of light required for removal of photolabile blocking groups and which may be functionalized for the attachment of monomers, may be advantageously used with the present invention depending on the nature and identity of the biomonomers used and the biopolymers desired.

A photolithographic mask 530 is placed adjacent the second side 532 of the substrate member 524. The mask 530 has opaque portions 534 and transparent portions 536. The opaque portions 534 correspond to the areas of the substrate member 524 which will not be photolabilized and the transparent portions 536 correspond to those areas which will be photolabilized. The opaque portions 534 of the mask 530 may, as shown, be circular and aligned in a close packed hexagonal arrangement to maximize the usable space on the substrate member 524 while maintaining the border areas. However, it should be noted that the opaque portions 534 may be of any convenient shape and arrangement.

A source of light 538 is placed on the opposite side of the mask 530 from the substrate member 524. The source of light generally comprises an ultraviolet lamp 540 which produces light of a wavelength sufficient to labilize a photolabile group. A filter 542 may also be placed between the lamp 540 and the mask 530 in order to remove other wavelengths of light which may be otherwise damaging to the chemical moieties of the array. The light is distributed across the mask 530 in a substantially uniform and collimated manner. As noted above, a laser or focused light beam might also be used for sequential illumination of the cells of the array.

In the practice of the invention using the flow cell 510, the substrate member 524 is initially treated to provide a linking group on the one side 526 which will form, along with the cavity 514, a portion of the reaction chamber 528. The substrate member 524 is then placed onto the base member 512 and aligned with the substrate alignment members 544. The substrate member 524 is secured to the base member 512 by clamps 546 and screws 548. The mask 530 is then placed on the second side 532 of the substrate member 524, aligned with the mask alignment members 550, and secured to the base member 512 by clamps 552 and screws 554. The repeatable alignment of the substrate member 524 and the mask 530 is very important in the practice of this invention using the flow cell 510. As was discussed above with respect to FIGS. 3 and 4, the improper or unrepeatable alignment of the mask 530 with respect to the substrate member 524 will lead to increased background noise in the use of the final array. Therefore, it is important to be able to repeatably align the mask 530 and the substrate member 524. It will be recognized by a practitioner of the art that the present illustration is not the only effective means of repeatably aligning the mask 530 and the substrate member 524. In the present illustration, the mask 530 is held substantially in contact with the second side 532 but it is not strictly necessary to do so. However, as the mask 530 is moved away from the substrate member 524, the light from the source 538 becomes diffuse as it falls upon the substrate member 524.

Once the flow cell 510 is fully assembled, it is connected to sources of reagents for preparing the array, such as an automated DNA or peptide synthesizer (not shown). The reaction chamber 528 is initially filled with a solution containing a compound which has two functional sites. One site is reactive with the linking group on the one side 526 of the substrate member 524 and the other site is protected with a photolabile protecting group. This compound may, in some cases, consist of an initial biomonomer or biomonomer analog where its presence in each member of the array as well as the border areas does not substantially degrade the performance of the array. The compound reacts with the linking groups and the residual solution is then rinsed from the reaction chamber 528. The light source 538 is then activated and the exposed photolabile groups are lost from the substrate member 524 and are taken up by the solution in the reaction chamber 528. Again, the chamber 528 is rinsed. A solution having a non-photolabile blocking group is then introduced into the chamber 528. The blocking group reacts with the non-protected linking groups on the substrate member 524 forming the boundary areas of the array. The blocking group solution is also rinsed out of the chamber 528.

The first mask 530 is then removed and second mask 530 having a different pattern of transparency and opacity is aligned and secured to the base member 512. The light source 538 is then activated and the exposed photolabile groups are lost from the substrate member 524 and are taken up by the solution in the reaction chamber 528. Again, the chamber 528 is rinsed. A solution having the first selected biomonomer is then introduced into the chamber 528. The biomonomer reacts with the non-protected groups on the substrate member 524 forming the first layer of biomonomers at the selected sites of the array. The biomonomer solution is then also rinsed out of the chamber 528. The process is repeated in a manner similar to that illustrated in FIG. 4. Additional reagents, as required by the oligomer synthesis, are added and removed from the chamber 528 at each step and the result is a solid-state micro-scale biopolymer array.

Therefore, an array prepared according to the present invention does not suffer the effects that limit the usability of arrays prepared according to prior art methods. The present invention provides for the preparation of micro-scale solid-state arrays. These arrays may contain tens of thousands of cells in a matrix less than 2 cm on a side. In addition, the micro-scale arrays of the present invention do not suffer the boundary effects of prior art arrays. The background noise is minimized since each cell in the array contains only that polymer which was designed to be there.

Arrays prepared in accordance with the present invention will provide discrete cells of substrate for the attachment of biomonomers. There will be substantially no boundary effect in such arrays.

The features of the invention which are believed to be new are set forth in the appended claims.

What is claimed is:

1. A nucleoside consisting of:

a saccharide selected from the group consisting of ribose and deoxyribose;

a basic group selected from the group consisting of purines and pyrimidines attached to the saccharide at the 1'-position of the saccharide; and a photolabile protecting group protecting the 5'-O-position of the saccharide wherein the photolabile protecting groups contains an ortho-nitrobenzyl moiety and a hydrogen atom on the alpha-carbon atom of the moiety.

2. The nucleoside of claim 1 wherein the purine or pyrimidine is selected from the group consisting of adenine, cytosine, guanine, thymine, uracil, and derivatives thereof.

3. The nucleoside of claim 2 wherein the photolabile protecting group is selected from the group consisting of 2-nitrobenzyl, 2-nitrobenzyloxycarbonyl and 6-nitroveratryloxycarbonyl.

4. A nucleoside having the following structure:

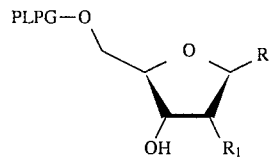

wherein R is a purine or a pyrimidine group, $R_1$ is hydrogen or an OH group, and PLPG is a photolabile protecting group containing an ortho-nitrobenzyl moiety and a hydrogen atom on the alpha-carbon atom to the moiety.

5. The nucleoside of claim 4 wherein the purine or pyrimidine group is selected from the group consisting of adenine, cytosine, guanine, thymine, uracil, and derivatives thereof.

6. The nucleoside of claim 5 wherein the photolabile protecting group is selected from the group consisting of 2-nitrobenzyl, 2-nitrobenzyloxycarbonyl and 6-nitroveratryloxycarbonyl.

* * * * *

UNITED STATES PATENT AND TRADEMARK OFFICE
CERTIFICATE OF CORRECTION

PATENT NO. : 5,556,961
DATED : September 17, 1996
INVENTOR(S) : Robert S. Foote et al.

It is certified that error appears in the above-indentified patent and that said Letters Patent is hereby corrected as shown below:

Column 2, between lines 55 and 56, insert the heading:
--SUMMARY OF THE INVENTION--.
Column 6, line 28, after "moiety" insert --is--.
Column 8, line 31, change "hag" to --has--.
Column 9, line 16, change "3-1, 3-2, and 3-3 are is" to --3A, 3B and 3C are--.
Column 9, line 20, change "4-1, 4-2, 4-3, and 4-4 are is" to --4A, 4B, 4C and 4D are--.
Column 9, between lines 27 and 28, insert the heading:
--DETAILED DESCRIPTION OF THE INVENTION--.
Column 9, line 32, change "thyroidinc" to --thymidine--.
Column 10, line 38, change "4-1, 4-2, 4-3, and 4-4" to --4A, 4B, 4C and 4D--.
Column 10, line 39, change "3-1, 3-2, and 3-3" to --3A, 3B and 3C--.
Column 11, line 2, change "FIG. 3" to --FIGS. 3A, 3B and 3C--.
Column 11, line 29, change "4-1, 4-2, 4-3, and 4-4" to --4A, 4B, 4C and 4D--.

Signed and Sealed this

Sixth Day of May, 1997

Attest:

BRUCE LEHMAN

*Attesting Officer*                *Commissioner of Patents and Trademarks*